United States Patent [19]

Porter

[11] Patent Number: 5,740,807
[45] Date of Patent: Apr. 21, 1998

[54] SUSPENDED ULTRA-SOUND INDUCED MICROBUBBLE CAVITATION IMAGING

[75] Inventor: Thomas R. Porter, Omaha, Nebr.

[73] Assignee: The Board of Regents of the University of Nebraska, Lincoln, Nebr.

[21] Appl. No.: 721,507

[22] Filed: Sep. 26, 1996

Related U.S. Application Data

[63] Continuation of Ser. No. 439,619, May 12, 1995, Pat. No. 5,560,364.

[51] Int. Cl.$^6$ ........................................................ A61B 8/00
[52] U.S. Cl. ........................................................ 128/662.02
[58] Field of Search ........................ 128/660.06, 660.07, 128/662.02; 424/9.5, 9.51, 9.52, 450

[56] References Cited

U.S. PATENT DOCUMENTS

| | | |
|---|---|---|
| 4,572,203 | 2/1986 | Feinstein . |
| 5,040,537 | 8/1991 | Katakura . |
| 5,255,683 | 10/1993 | Monaghan ..................... 128/662.02 |
| 5,380,519 | 1/1995 | Schneider et al. ................ 128/662.02 |
| 5,410,516 | 4/1995 | Uhlendorf et al. . |
| 5,413,774 | 5/1995 | Schneider et al. . |
| 5,567,415 | 10/1996 | Porter ................................ 128/662.02 |

OTHER PUBLICATIONS

Putterman, "Sonoluminescence: Sound into Light", *Scientific American*, Feb. 1995, pp. 47–51.

*Primary Examiner*—George Manuel
*Attorney, Agent, or Firm*—Zarley, McKee, Thomte, Voorhees, & Sease

[57] ABSTRACT

An ultrasonic imaging technique is disclosed which uses microbubbles as echo contrast agents. In general the method employs maitenance of an ultrasound signal while the contrast agent is intravenously injected into a mammal. Once all the contrast agent has been injected and transmission of the signal is suspended for a period of time sufficient for the microbubbles perfuse the organ of interest. Transmission of the ultrasound signal is then resumed and peak contrast images are obtained which rival more complicated imaging procedures such as nuclear resonance imaging.

19 Claims, No Drawings

SUSPENDED ULTRA-SOUND INDUCED MICROBUBBLE CAVITATION IMAGING

This is a continuation of application Ser. No. 08/439,619 filed on May 12, 1995 now U.S. Pat. No. 5,560,364.

BACKGROUND OF THE INVENTION

Ultrasonic imaging is used as a diagnostic tool to aid in therapeutic procedures. It is based on the principle that waves of sound energy can be focused upon an area of interest and reflected to produce an image. Generally, an ultrasonic transducer is placed on a body surface overlying the area to be imaged, and ultrasonic energy, produced by generating and receiving sound waves is transmitted. The ultrasonic energy is reflected back to the transducer where it is translated into an ultrasonic image. The amount and characteristics of the reflected energy depend upon the acoustic properties of the tissues, and contrast agents which are echogenic are preferentially used to create ultrasonic energy in an area of interest and improve the image received.

In ultrasound imaging, videotape images obtained following contrast injection are digitized, allowing the gray scale to be quantified from 1 to 225 gray scale units for 30 cardiac cycles. The contrast intensity is plotted on the vertical axis against time on the horizontal axis. The peak videointensity (corrected for baseline intensity) is determined as the highest point on the time intensity curve.

For a discussion of contrast echographic instrumentation, see, for example, De Jong N, "Acoustic properties of ultrasound contrast agents", CIP-GEGEVENS KONINKLIJKE BIBLIOTHEEK, DEN HAG (1993), pages 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

A multiplicity of potential ultrasonic imaging agents has been reported for contrast echocardiography. No such agent routinely attains visually discernible myocardial uptake following peripheral intravenous injection. Although there have been many reports of transpulmonary transmission of ultrasound contrast agents following intravenous injection and despite the fact that myocardial opacification on echocardiogram can be produced by left sided injection of such contrast agents, visualization of myocardial contrast has not been achieved by intravenous administration of sonicated microbubbles.

Most recently, sonicated albumin and sonicated dextrose/albumin have been shown to produce variable degrees of left ventricular chamber ultrasound contrast following intravenous injection. (See Villanueva et al. Circulation 85:1557–1564, 1992; Linet al. Int j Card Imaging 8:53–6, 1992; Feinstein et al. J Am Coll Cardiol 16:316–224, 1990; Keller et al. Am Heart J 114:570–575, 1987; and Shapiro et al. J Am Coll Cardiol 16:1603–1607, 1990). The microbubbles of these contrast agents are small (4–6 microns and are capable of swift transpulmonary passage. However, visually discernible myocardial uptake of such microbubbles following peripheral intravenous injection has not been possible because of the rapid diffusion of blood soluble oxygen and nitrogen inside the microbubble into the blood which consequently loses its ultrasound reflective properties (e.g., see Porter et al. J Am Soc Echocard Supplement 7:S1, May 1994, and Weyman A E: Principles and Practice of Echocardiography, Malvern, Pa.: Lea & Febiger, 1994; pp. 302–26.)

Despite recent advances in contrast agents comprising injectable gas encapsulated microbubbles, several problems remain for adequate detection and visualization of the organ of interest. The bubbles are plagued with filtration by capillaries, diffusion of gas to the liquid medium, and lack of concentration at the organ of interest due to dilution.

Attempts to solve these problems have led to studies of acoustic velocity of media containing gas bubbles, second harmonic emission, and resonance frequency. These studies to date have met with little improvement in contrast visualization.

It is an object of the present invention to provide a safe, simple and effective method to visualize and improve an ultrasound image following injection of gas-filled microbubbles.

Other objects of the invention will be apparent from the description of the invention which follows.

SUMMARY OF THE INVENTION

According to the invention, after introduction of a microbubble contrast agent the ultrasound transmission is suspended to allow the contrast agent to perfuse the organ of interest and is then resumed for a striking improvement in contrast. Use of this method results in up to ten times improvement in contrast, decreases acoustic shadowing and allows for reduction in the amount of contrast agent necessary, thereby reducing toxicity and improving safety.

DETAILED DESCRIPTION OF THE INVENTION

The primary problem in contrast ultrasound imaging is the detection and quantification of perfusion in the anatomical organs of interest, such as heart, kidney, liver etc. The most success to date has been with using contrast gas-filled microbubbles which are injected intravenously into the bloodstream.

Often, however, the intravenously injected bolus of microbubbles gets diluted in concentration as it travels to the targeted organ of interest, making detection difficult if not impossible. One of the primary problems in echocardiography is the detection of myocardial perfusion. More importantly, as the bolus flows through the right-side of the heart and passes through the lungs, microbubbles greater than 8 microns in size are filtered out by the pulmonary capillaries.

Further, as the bubbles flow into the left-side of the heart, some of the bubbles are destroyed during the course of the heart cycle as they are subjected to the fairly high systolic pressures in the left ventricle (LV). Some of the bubbles disappear by the simple process of diffusion of gas into the surrounding liquid medium.

Finally, the bubbles in the ventricle strongly attenuate the incident ultrasound field and cast an acoustic shadow on the distal myocardium. Hence, there is a trade-off between increasing the dose for improved microbubble detection sensitivity and the need for minimizing the acoustical shadowing of the myocardial beds. All of this is exacerbated by the fact that only about 4% of the total blood volume in the LV cavity enters the coronary circulation. As a net result, only a small number of microbubbles of small size (from the original bolus injection) traverse the myocardial vasculature.

This invention alleviates these concerns by allowing for detection of very small amounts of contrast agent, improving contrast by as much as ten times and can be used in echocardiography as well as for renal or hepatic imaging. The invention (suspended ultrasound induced cavitation imaging) comprises a modification of standard ultrasound imaging techniques and can be used with any ultrasound imaging device in combination with a microbubble contrast agent.

In this method the ultrasound signal is operating (i.e. the transucer is held in position over the organ of interest, for example the heart) upon introduction of the contrast agent. The contrast agent is then injected peripherally, in an amount sufficient for visual detection of the organ of interest. Standard amounts of microbubble contrast agent may be used, from about 0.04 ml/kg to about 0.08 ml/kg for humans however it will be seen that much smaller amounts will work equally as well with the method of the invention, as little as 0.001 ml/kg to 0.0025 ml/kg. The dose range is patient specific as large patients may require slightly higher doses to produce equivalent left ventricular contrast. Standard methodology for contrast echocardiography are described in Weyman, Arthur E. "Principles and Practice of Echocardiography" Lea and Fibiger, Malvern, Pa. (1994 2d Ed).

After injection the transmission of the ultrasound signal is interrupted, or suspended for a period of time sufficient for the contrast agent to perfuse the organ of interest. The time period will generally vary according to the organ of interest. It must only be long enough for some of the agent to have reached the organ of interest. For the heart this would be the time sufficient for the contrast agent to reach the myocardium. This is approximately about 10–120 seconds, preferably around 20–30 seconds and should not vary significantly from patient to patient.

The length of time for other organs or for any particular patient may be easily ascertained by conducting standard ultrasound imaging where the transmission is not interrupted and timing the period from injection to perfusion of the organ of interest.

Once the microbubbles have reached the organ of interest or myocardium for echocardiography, the transmission of the ultrasound signal is resumed and peak myocardial contrast images are obtained.

In echocardiography there will be a uniform opacification of the entire myocardium. Within a few seconds, the intensity of the entire myocardium uniformly drops to the original (dark) intensity level. Regions of the myocardial bed that are devoid of blood flow and contrast remain dark at all times. Hence, it is easy to differentiate between normally perfused and abnormally perfused myocardial regions.

While not wishing to be bound by any theory, it is postulated that the observed phenomenon arises as a result of the transient response of the contrast microbubbles when subjected to a driving ultrasonic field. The ultrasound signal causes the microbubbles to compress, or cavitate. When the microbubbles are injected, they become compressed, as they encounter the ultrasonic field. When the ultrasound signal is suspended, the transmit power into the anatomy is shut off. In the absence of a radiating field, the microbubbles in the myocardium or other organ, grow in size by a finite amount. Some may even coalesce to form larger scatterers.

The reflection of the ultrasound signal will then be enhanced by the larger size of the microbubbles. This is because the backscattered ultrasound energy is directly proportional to the number of scatterers in the region of interest and varies as the sixth power of the radius of the scatterer.

When the ultrasound system is resumed, the transmit power into the anatomy is enabled and will generate the image scan on the display. Peak contrast images are obtained at this point, before the ultrasound signal begins to cavitate the microbubbles once again. As the ultrasound field builds up from zero to steady state, the pressure on the microbubbles increases causing them to diminish in size once again. This transient decrease in scatterer size causes the resultant transient decrease in myocardial intensity.

It is postulated that another explanation for the increase in intensity upon resuming ultrasound transmission may be that the impressed ultrasound field sputters the microbubbles and any coalesced microbubble aggregates into numerous microbubbles thereby effectively increasing the number of scatterers and thereby causing the increased myocardial opacification. The contrast is so improved that the image produced rivals that of more complicated imaging such as nuclear resonance imaging.

The main advantage of this invention is that it allows for sensitive detection and quantification of perfusion at the target organ in a non-invasive mode using a very small dose of contrast microbubbles without producing acoustical shadows. Because of the small dose, patient safety is enhanced and the cost is also minimized.

For most ultrasound imaging, the contrast agent is formulated in a pharmaceutically effective dosage form for peripheral administration to the host to be imaged. Generally such host is a human subject although other mammalian hosts, such as canine or equine can be imaged effectively. In a most preferred embodiment the contrast agent is a sonicated mixture of commercially available albumin (human), USP, solution (generally supplied as 5% or a 25%, by weight, sterile aqueous solutions), and commercially available dextrose, USP, for intravenous administration are employed. This mixture is sonicated under ambient conditions, i.e., room air, temperature and pressure, and is perfused with perfluorocarbon or other commercially available inert gas (99.9% by weight) during sonication.

In a preferred embodiment the invention uses a microbubble contrast agent wherein the microbubbles are stabilized by a filmogenic, de-naturable protein coating. Suitable proteins include naturally occurring proteins such as albumin, human gamma-globulin, human apotransferrin, Beta-lactose, and urease. The invention preferably employs a naturally occurring protein, but synthetic proteins may also be used. Particularly preferred is human serum albumin.

Although intravenous echo contrast agents made from sonicated microbubbles are known (e.g., ALBUNEX, Molecular Biosystems, Inc.) and can be employed in this invention, it is preferred to use a sonicated aqueous solution containing a mixture of a pharmaceutically acceptable saccharide, e.g., dextrose, and a protein, e.g., albumin. Generally, sonication is performed in an air atmosphere. In an especially preferred embodiment, dextrose, which is readily available in pharmaceutically acceptable dosage forms, is the preferred saccharide and human serum albumin is the preferred protein. The preferred embodiment would include a two-fold to eight-fold dilution of 5%–50% by weight of dextrose and a 2%–10% by weight of human serum albumin. Exemplary of other saccharide solutions of this invention are an aqueous monosaccharide solution (e.g. having the formula $C_6H_6O_{12}$, such as, the hexoses, dextrose or fructose, or mixtures thereof), aqueous disaccharide solution (e.g., having the formula $C_{12}H_{22}O_{11}$, such as sucrose, lactose or maltose, or mixture thereof), or aqueous polysaccharide solution (e.g., soluble starches having the formula $(C_6H_{10}O_5)n$, wherein n is a whole integer between about 20 and about 200, such as amylose or dextran, or mixtures thereof. Sonication by ultrasonic energy causes cavitation within the dextrose-albumin solution at sites of particulate matter or gas in the fluid. These cavitation sites eventually resonate and produce small microbubbles (about 4 to about 7 microns in size) which are non-collapsing and stable. In general, sonication conditions which produce concentrations of greater than about $4 \times 10^8$ m of between about 5 and about 6 micron microbubbles are preferred.

The mean microbubble size of sonicated dextrose albumin ranges from between about 5 to about 6 microns. This is a good size as it has been observed that microbubble radius decreases as a function of time in a still liquid due to a diffusion gradient present between the internal and external gases of the microbubble. An increase in microbubble size has a significant effect on the persistence of a microbubble within blood. It must also be of a size sufficient for transpulmonary passage. It must have a mean diameter of less than 10 microns and greater 0.1 microns. Since the size of albumin microbubbles is ideal (between 5 and 6 microns) for transpulmonary passage, the major reason for the significant loss in left ventricular and myocardial videointensity produced following intravenous injection of albumin coated microbubbles is due to the significant diffusion of gases within the microbubble following intravenous injection during transit to the left ventricular cavity. Sonicated dextrose albumin enhanced with an inert gas such as perfluorocarbon gas, having a lower blood solubility than air, and a molecular weight of greater than 100 grams/mole, produces a significantly higher left ventricular and myocardial videointensity than sonicated albumin alone.

Because of high surface tension, the concentration of nitrogen and oxygen gas within the microbubble is much higher than that in blood, and thus there is a rapid diffusion of this gas into the blood stream following intravenous injection. Wible et al. (Circulation, 88:I-401, 1993) have demonstrated that this diffusion process can be accelerated if one decreased the partial pressure of nitrogen within the blood stream by decreasing the inhaled fraction of nitrogen. This lower external concentration of nitrogen results in loss of the left ventricular videointensity produced by the same intravenous injection of sonicated albumin while inhaling room air. It has also been observed that oxygen rapidly diffuses out of gas bubbles into human blood (See Yang et al., J Biomech 3:275, 1971).

Both nitrogen and oxygen diffuse rapidly across these concentration gradients, but nitrogen appears to dissolve more slowly than oxygen into blood. Since nitrogen is the major component of air, decreasing the concentration gradient for nitrogen across the microbubble improves left ventricular and myocardial videointensity following intravenous injection. Exposing the microbubbles to a non-toxic gas having a lower blood solubility and/or microbubble diffusivity than that of nitrogen and having a gas density of greater than about 0.300 lb/ft$^3$ during sonication increases the size and stability of the microbubbles in sonicated dextrose albumin, while lowering the solubility and diffusivity of the microbubbles in blood. Suitable gases are those which are gas at 37° C. and which are nontoxic, insoluble gases useful for contrast agents include but are not limited to prefluorocarbon gases such as perfluoromethane, perfluoroethane, perfluoropropane, perflouorobutane, perfluoropentane etc, or sulfur hexafluoride. In a preferred embodiment the gas is perfluoropropane ($C_3F_8$) or perfluorobutane ($C_4F_{10}$). The perfluorocarbon gas content of the microbubbles is sufficient to lower microbubble gas solubility and diffusivity in vivo in blood. Generally, the minimum amount of insoluble gas in the microbubbles which is effective is that amount which results in microbubbles which pass reliably through the pulmonary circulation without collapse. This is evidenced by opacification of the myocardium of the left ventricle of the heart following intravenous injection and can be visually discerned by echocardiography.

In addition to myocardial imaging the contrast agents of this invention are useful for renal and hepatic imaging. Thus, another embodiment of this invention provides a method for myocardial, renal or hepatic opacification. The method preferred involves obtaining an echo contrast agent of this invention, introducing said echo contrast agent into a host by intravenous injection, and performing an echo contrast study on said host using a suitable Doppler or ultrasound echo apparatus as discussed more fully hereinafter.

In a most preferred embodiment the contrast agent is a perfluorobutane-enhanced sonicated dextrose albumin solution comprised of a sonicated three-fold dilution of 5% human serum albumin with 5% dextrose. During sonication, said solution is perfused with perfluoropropane for about 80 seconds, and concomitantly exposed to perfluorobutane or perfluoropropane for at least about 5 seconds during sonication. This lowers the solubility and diffusivity of the microbubble gas. The resulting microbubbles are concentrated at room temperature for at least about 120±5 minutes, wherein the excess solution settles in the sonicating syringe. The excess solution is expelled and the concentrated microbubbles are transferred to a sterile syringe and injected intravenously into a mammal.

Using the method of the invention in echocardiography will result in a higher degree of myocardial opacification, endocardial border delineation, and enhanced detection of left-sided ultrasound Doppler signals, upon peripheral venous administration. Additionally, the method of the invention allow for increased sensitivity as small doses of microbubbles are easily detected, which subsequently enables ultrasonic visualization of the liver and kidneys following an intravenous injection.

The following examples are for illustration purposes only and are in no way intended to limit the invention. It will be apparent to those of skill in the art that other embodiments are practicable and even intended.

EXAMPLE 1

Preparation of Contrast Agents

Albumin (human) USP, 5% solution (hereinafter referred to as "albumin") and dextrose USP, 5% solution (hereinafter referred to as "dextrose") were obtained from a commercial source. The sonicating system used for sonication was a Heat System Ultrasonic Processor Model XL2020 (Heat Systems Inc., Farmingdale, N.Y.). The ½ inch horn transducer was a resonating piezoelectric device. The ½ inch sonicating horn tip was sterilized prior to each sonication.

Sonication of Samples

Sixteen milliliter aliquots of albumin diluted 1:3 with dextrose were drawn up into a 35 cc "Monoject" syringe (Becton Dickinson and Company, Rutherford, N.J.) and sonicated for 80±1 seconds. The "Leur-Lok" of the 35 milliliter syringe is then attached to a stopcock. After mixing the dextrose albumin solution by hand for about 7 to about 10 seconds, the plunger was removed from the top of the syringe. The sterile sonicating horn was then lowered into the open end of the syringe until at the surface of the albumin-dextrose solution. The solution was placed at the horn tip and manually held at this position while continuously sonicating at a frequency of 20,000 Hz and a power output of 210 W for 80±1 seconds to form a stable microbubble solution.

Gas Perfusion of Samples

During sonication, the dextrose albumin mixture was exposed to either perfluorobutane or perfluoropropane gas (Commercial Grade, 99.9% by weight). The gas was drawn up into a sterile syringe through a 0.22 µM filter (Micron Separations Inc., Westborough, Mass.) to prevent contamination. During sonication, 5 milliliters of the perfluorocarbon gas was manually injected into the solution, over the 80 second time interval, through the stopcock so that the microbubbles produced contained this less soluble gas. The total volume of perfluorobutane-enhanced sonicated dextrose albumin (BESDA) or perfluoropropane-enhanced sonicated dextrose albumin (PESDA) produced with this formulation was 25±2 milliliters. These samples were then used for intravenous injection.

Microbubble Analysis

Microbubble size and purity was determined using hemocytometry. Microscopic inspection of the microbubbles was performed to determine if any coalescent microbubbles were present in the solution. Microbubble concentration was determined using a Coulter Counter. The contrast agent was rejected for use if any of the following conditions were present: the mean microbubble size is 4.0 to 6.0 microns; coalesced microbubbles or strands were detected by light microscopy; or the mean microbubble concentration was less than $0.8 \times 10^9$ or greater than $1.5 \times 10^9$ microbubble/milliliter. The sample was also rejected if the number of microbubbles greater than 10 microns in the sample was greater than 4%.

All samples were stored in 35 milliliter syringes until time of injection. All solutions were given within 36 hours of production. All samples were prepared in a laminar flow hood.

EXAMPLE 2

Preparation of Open-Chest Dogs

Mongrel dogs of either sex (15–30 kilograms) were anesthetized with sodium pentobarbital (30 milligram per kilogram intravenously), intubated, and ventilated initially with room air using a positive pressure respirator. A left thoracotomy was performed under sterile conditions and the pericardium incised. In addition to a 19 gauge peripheral intravenous line, eight French Catheters were placed in the femoral artery and vein for intravenous administration of ultrasound contrast agents and pressure monitoring. Through one femoral venous sheath, a 7F balloon-tipped thermodilution catheter was placed in the pulmonary artery using fluoroscopy for determination of pulmonary artery pressure and cardiac output. A 7F pigtail catheter was introduced into the left ventricle for pressure measurements (left ventricular systolic and end-diastolic pressure) following injection of each ultrasound contrast agent.

Following adequate surgical exposure, a 3.5 Megahertz ultrasound transducer connected to a commercially available ultrasound scanner (Hewlett Packard Company; Andover, Mass.) was placed in a warm water bath. The bath overlays the anterior epicardial surface. The transducer was mounted on a clamp and lowered into the bath. It was adjusted until an optimal stable short axis view of the left and right ventricle had been obtained at the ventricular mid-papillary muscle level. These images were then used to assess left ventricular cavity and myocardial uptake of contrast following intravenous injection.

EXAMPLE 3

Delayed Ultrasound-Induced Cavitation Imaging vs. Conventional Ultrasound Imaging for Echocardiography To determine if the acoustic shadowing could be decreased or eliminated with the method of the invention, four human patients were tested comparing conventional ultrasound imaging with delayed ultrasound-induced cavitation imaging. For this experiment, myocardial contrast was determined using on-line digitally acquired videointensity obtained from software supplied in conjunction with the commercially available ultrasound system (Hewlett-Packard Sonos 1500 Phased Array imaging system, Hewlett Packard, Andover, Mass.). The peak myocardial videointensity (PMVI), duration of acoustic shadowing (AS), and percent of myocardial contrast (MC) were observed. The results are shown in Table 1 below.

Each patient was injected intravenously with 0.0025–0.005 milliliter per kilogram of contrast agent, prepared as in Example 1. The fluorocarbon gas agent used was decafluorobutane. For the conventional ultrasound imaging, the transmission of ultrasound was constant at 2.5–2.7 MHz and imaging was performed continuously throughout the experiment. Peak contrast images of the myocardium were obtained once the microbubbles of the contrast agent reached the myocardium.

For the delayed ultrasound-induced cavitation imaging, the transmission of ultrasound was maintained at 2.5–2.7 MHz until the patient was injected with contrast agent. Upon intravenous injection of contrast agent, the ultrasound transmission was suspended for 20 to 30 seconds. Ultrasound transmission was resumed at 2.5–2.7 MHz once the microbubbles of the contrast agent reached the myocardium. Peak myocardial contrast images were obtained immediately following commencement of the ultrasound transmission and before the microbubbles began to compress.

TABLE 1

| | | | Myocardial Contrast in Ultrasound Imaging | | | |
|---|---|---|---|---|---|---|
| Imaging Modality | Patient # | Dose of Contrast Agent | Ultrasound Signal Delay Time | PMVI | Acoustic Shadowing (AS) | Myocardial Contrast (MC) |
| UIC* | 1) 2.7 MHz | 0.005 | 20 | 19 | 10 sec | 2+ |
| | 2) 2.5 MHz | 0.0025 | 20 | 11 | 23 sec | 2+ |

TABLE 1-continued

Myocardial Contrast in Ultrasound Imaging

| Imaging Modality | Patient # | Dose of Contrast Agent | Ultrasound Signal Delay Time | PMVI | Acoustic Shadowing (AS) | Myocardial Contrast (MC) |
|---|---|---|---|---|---|---|
| | 3) 2.5 MHz | 0.0025 | 25 | 1 | 8 sec | 1+ |
| | 4) 2.5 MHz | 0.005 | 30 | 14 | 12 sec | 2+ |
| CONV** | 1) 2.7 MHz | 0.005 | 0 | 5 | 20 sec | 2+ |
| | 2) 2.5 MHz | 0.0025 | 0 | 0 | 25 sec | 1+ |
| | 3) 2.5 MHz | 0.0025 | 0 | 3 | 20 sec | 1+ |
| | 4) 2.5 MHz | 0.005 | 0 | 3 | 30 sec | 2+ |

*delayed ultrasound induced cavitation
**conventional ultrasound imaging

The results of this experiment indicate that conventional imaging following intravenous injection of the perfluorocarbon-enhanced sonicated dextrose albumin contrast agent produced a high degree of acoustic shadowing in the posterior structures of the left ventricular cavity. The delayed ultrasound-induced cavitation imaging decreased the amount of acoustic shadowing by a sufficient amount to enable the imaging of inferior defects of the myocardium. The method of the invention was also compared to standard myocardial imaging in dogs with an increase in myocardial contrast of ten times that of conventional method. A marked reduction in acoustic shadowing was also seen.

EXAMPLE 4

Effects of Transducer Frequency and Power on Cavitation Ultrasound Imaging

The effects of transducer frequency and transducer acoustic output was demonstrated in the method of the invention using two open chest dogs.

Two dogs received a total of 22 intravenous injections of a perfluoropropane-enhanced sonicated dextrose albumin contrast agent (prepared as in Example 1) at doses between 0.005 and 0.010 milliliters per kilogram body weight. The diagnostic ultrasound signal was transmitted only after the contrast agent microbubbles had reached the myocardium and peak myocardial videointensity (PMVI) and the duration of myocardial contrast (dur-MC) were measured following each injection. The transducer frequency and acoustic output were varied between each injection. The results are shown in Table 2 below.

TABLE 2

Effects of Transducer Frequency and Power on Cavitation Ultrasound Imaging

| Transducer Frequency (MHZ) | Acoustic Output (decibels) | PMVI | Duration of myocardial contrast (dur-MC) |
|---|---|---|---|
| 2.0–2.5 | 158–170 | 42 ± 6 | 5 ± 1* |
| 2.0–2.5 | 212 | 43 ± 6 | 1 ± 1* |
| 2.7–3.5 | 158–170 | 37 ± 7 | 11 ± 1** |
| 2.7–3.5 | 212 | 31 ± 7 | 3 ± 1 |

*p < 0.05, compared to other transducer frequencies
**p < 0.05, compared to other durations The results indicate that the best myocardial contrast imaging is obtained when the transducer frequency is low and a low acoustic output prolongs the duration of this phenomenon.

What is claimed is:

1. A method of ultrasonic myocardial, renal, or hepatic imaging which employs an echo contrast agent having microbubbles comprising:
   introducing said echo contrast agent into an animal by intravenous injection;
   suspending ultrasonic transmission for a time sufficient for said contrast agent to perfuse an organ of interest and thereafter;
   resuming ultrasonic transmission.

2. A method of ultrasonic myocardial, renal, or hepatic imaging which employs an echo contrast agent having microbubbles comprising:
   introducing said echo contrast agent into an animal by intravenous injection;
   altering ultrasonic transmission so that microbubble cavitation is decreased by decreasing the ultrasonic field encountered by said bubbles until said bubbles or a majority thereof perfuse the organ of interest and thereafter;
   resuming ultrasonic transmission to visualize said organ.

3. The method of claim 2 wherein said animal is a dog and said step of introducing contrast agent is in an amount of from about 0.005 ml/kg to about 0.030 ml/kg.

4. The method of claim 2 wherein said animal is a human and said step of introducing said contrast agent is in an amount of from about 0.001 ml/kg to about 0.0020 ml/kg.

5. The method of claim 2 wherein said step of introducing said echo contrast agent comprises:
   introducing a contrast agent with perfluorocarbon gas or other insoluble gas with a molecular weight of greater than 100 grams/mole encapsulated microbubbles.

6. The method of claim 5 wherein said perfluorocarbon gas is selected from the group consisting of perfluoromethane, perfluorobutane, perfluoroethane, and perfluoropropane or a blood insoluble gas with a molecular weight of greater than 100 grams/mole.

7. The method of claim 6 wherein said perfluorocarbon gas is perflurobutane.

8. The method of claim 2 wherein said microbubbles are encapsulated by a filmogenic protein such as human serum albumin.

9. The method of claim 8 wherein said human serum albumin is diluted with dextrose.

10. The method of claim 9 wherein said dilution of human serum albumin with dextrose is three to one.

11. The method of claim 9 wherein said human serum albumin is a 5% by weight solution and said dextrose is a 5% by weight solution.

12. The method of claim 2 wherein said altering ultrasonic transmission is for a time period of approximately of 10–120 seconds.

13. A method of ultrasonic myocardial, renal, or hepatic imaging which employs an echo contrast agent having microbubbles comprising:

introducing said echo contrast agent into an animal by intravenous injection;

decreasing ultrasonic energy transmission so that microbubble cavitation is decreased thereby increasing the size and number of said microbubbles to increase back scattered ultrasound energy, and thereafter;

resuming ultrasonic transmission once said bubbles or a majority of said bubbles perfuse the organ of interest at levels sufficient to visualize said organ.

14. A method of ultrasonic myocardial, renal, or hepatic imaging comprising:

preparing an echo contrast agent which comprises microbubbles;

introducing said echo contrast agent into an animal;

altering ultrasonic transmission so that microbubble cavitation is decreased so that the ultrasonic field encountered by said bubbles is decreased and until said bubbles or a majority thereof perfuse the organ of interest and thereafter, resuming ultrasonic transmission to visualize said organ.

15. The method of claim 14 wherein said step of altering transmission comprises: suspending ultrasonic transmission for a period of approximately 10 to approximately 30 seconds.

16. The method of claim 14 wherein said step of preparing said echo contrast agent includes the step of:

diluting a solution of 5% by weight albumin with 5% by weight dextrose by 3 to 1 to create a mixture.

17. The method of claim 16 further comprising the step of:

sonicating said mixture in the presence of a perfluorocarbon gas.

18. The method of claim 17 wherein said perfluorocarbon gas is selected from the group consisting of perfluoropropane and perfluorobutane.

19. The method of claim 18 wherein said perfluorocarbon gas is perfluorobutane.

* * * * *